US010496166B2

(12) United States Patent
Kimura et al.

(10) Patent No.: US 10,496,166 B2
(45) Date of Patent: Dec. 3, 2019

(54) EYE TRACKING DEVICE AND EYE TRACKING METHOD

(71) Applicant: Panasonic Intellectual Property Management Co., Ltd., Osaka (JP)

(72) Inventors: Soichi Kimura, Osaka (JP); Hidetoshi Takeda, Osaka (JP); Shingo Yamazoe, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/069,904

(22) PCT Filed: Feb. 13, 2017

(86) PCT No.: PCT/JP2017/005052
§ 371 (c)(1),
(2) Date: Jul. 13, 2018

(87) PCT Pub. No.: WO2017/179279
PCT Pub. Date: Oct. 19, 2017

(65) Prior Publication Data
US 2019/0025912 A1 Jan. 24, 2019

(30) Foreign Application Priority Data
Apr. 12, 2016 (JP) .................. 2016-079346

(51) Int. Cl.
G06F 3/01 (2006.01)
A61B 3/113 (2006.01)
G06K 9/00 (2006.01)
(52) U.S. Cl.
CPC .............. *G06F 3/013* (2013.01); *A61B 3/113* (2013.01); *G06K 9/00604* (2013.01)

(58) Field of Classification Search
CPC ....... A61B 3/0041; A61B 3/113; G06F 3/013; G06F 3/0346; G06K 9/00604
(Continued)

(56) References Cited

U.S. PATENT DOCUMENTS 9,514,538 B2 * 12/2016 Ebisawa ................. A61B 3/111
2010/0245767 A1 * 9/2010 Chao ...................... A61B 3/113
351/210

(Continued)

FOREIGN PATENT DOCUMENTS

JP 2010-259605 11/2010
WO 2012/020760 2/2012

OTHER PUBLICATIONS

International Search Report of PCT application No. PCT/JP2017/005052 dated May 9, 2017.
(Continued)

*Primary Examiner* — Tony O Davis
(74) *Attorney, Agent, or Firm* — Greenblum & Bernstein, P.L.C.

(57) ABSTRACT

An eye tracking method in the disclosure comprises an image-capturing step of capturing a facial image including an eyeball of an object person, light from a light source that emits the light to form a corneal reflex point on the eyeball of the object person who gazes at a predetermined gaze point being reflected from the eyeball, a detecting step of calculating visual line information in a world coordinate system using the facial image captured in the image-capturing step and a correcting step of transforming the visual line information in the world coordinate system calculated in the detecting step into visual line information in a correction coordinate system that is a coordinate system different from the world coordinate system, and correcting the visual line information in the correction coordinate system using cor- (Continued)

rection information for correcting a detection error caused by an individual difference of the eyeball.

17 Claims, 7 Drawing Sheets

(58) Field of Classification Search
USPC .................................................. 345/157, 633
See application file for complete search history.

(56) References Cited

U.S. PATENT DOCUMENTS

| | | | |
|---|---|---|---|
| 2013/0188834 A1* | 7/2013 | Ebisawa | A61B 3/113 382/103 |
| 2016/0095511 A1* | 4/2016 | Taguchi | A61B 3/0025 |
| 2017/0007120 A1* | 1/2017 | Shudo | A61B 3/113 |
| 2018/0032133 A1* | 2/2018 | Cho | G06F 3/013 |
| 2018/0235466 A1* | 8/2018 | Hakoshima | A61B 3/113 |
| 2018/0239427 A1* | 8/2018 | Hakoshima | A61B 3/113 |

OTHER PUBLICATIONS

Takehiko Ohno et al., "Just Look at Two Points: A Gaze Tracking System with Easy Calibration", Journal of Information Processing Society of Japan, Apr. 2003, vol. 44 No. 4, p. 1136-1149 (Partial Translation).

* cited by examiner

EYE TRACKING DEVICE AND EYE TRACKING METHOD

This application is a U.S. national stage application of the PCT International Application No. PCT/JP2017/005052 filed on Feb. 13, 2017, which claims the benefit of foreign priority of Japanese patent application No. 2016-079346 filed on Apr. 12, 2016, the contents all of which are incorporated herein by reference.

TECHNICAL FIELD

The present invention relates to an eye tracking device and an eye tracking method for correcting an individual difference of a visual line of an object person detected based on an eyeball image of the object person.

BACKGROUND ART

As a technique capable of measuring a visual line with high accuracy in a non-contact manner, a corneal reflection method has been known. This method uses reflected light on an eyeball, and therefore the accuracy is largely affected by the individual difference of an eyeball shape. Consequently, a measured visual line is corrected using an individual error.

PTL 1 discloses a gaze point detection device including a plurality of stereo cameras that obtain a facial image of an object person, a light source disposed outside an opening of the stereo camera, a control circuit, and an image processing device. The image processing device calculates an angle of a visual line of the object person by using a function based on the facial images, calculates a direction of the visual line while correcting the function such that directions of visual lines calculated corresponding to the plurality of stereo cameras are close to each other, and detects a gaze point of the object person on a display screen.

CITATION LIST

Patent Literature

PTL 1: WO 2012-020760

SUMMARY OF THE INVENTION

The present disclosure provides an eye tracking device that can calculate correction information about a visual line independently of a positional relationship between gaze points and improve detection accuracy of the visual line.

The eye tracking device of the present disclosure includes a light source, an image-capturing unit, a detector, and a correction unit. The light source emits light to form a corneal reflex point on an eyeball of an object person who gazes at a predetermined gaze point. The image-capturing unit captures a facial image including the eyeball of the object person, the light from the light source being reflected from the eyeball. The detector calculates visual line information in a world coordinate system using the facial image captured by the image-capturing unit. The correction unit transforms the visual line information in the world coordinate system calculated by the detector into visual line information in a correction coordinate system that is a coordinate system different from the world coordinate system based on a positional relationship between two gaze points of which positions are different from each other, and corrects the visual line information in the correction coordinate system using correction information for correcting a detection error caused by an individual difference of the eyeball.

In an eye tracking method of the present disclosure, a facial image including an eyeball of an object person is captured, light from a light source that emits the light to form a corneal reflex point on the eyeball of the object person who gazes at a predetermined gaze point being reflected from the eyeball. Then, visual line information in a world coordinate system is calculated using the captured facial image. Further, the calculated visual line information in the world coordinate system is transformed into visual line information in a correction coordinate system that is a coordinate system different from the world coordinate system based on a positional relationship between two gaze points of which positions are different from each other, and the visual line information in the correction coordinate system is corrected using the correction information for correcting a detection error caused by an individual difference of the eyeball.

According to the eye tracking device of the present disclosure, a freedom degree of a gaze destination can be increased, and detection accuracy can be improved.

DESCRIPTION OF EMBODIMENTS

Hereinafter, exemplary embodiments will be described in detail with reference to the drawings as appropriate. However, the detailed description more than necessary may be omitted. For example, the detailed description of already known matters and the overlapping description of the substantially same configuration may be omitted. The omission is aimed to prevent unnecessary redundancy of the following description, and to help those skilled in the art easily understand the following description.

Note that the attached drawings and the following description are provided for those skilled in the art to fully understand the present disclosure, and are not intended to limit the subject matter as described in the appended claims.

First Exemplary Embodiment

1. Configuration

[1-1. System Configuration]

Figure 1:
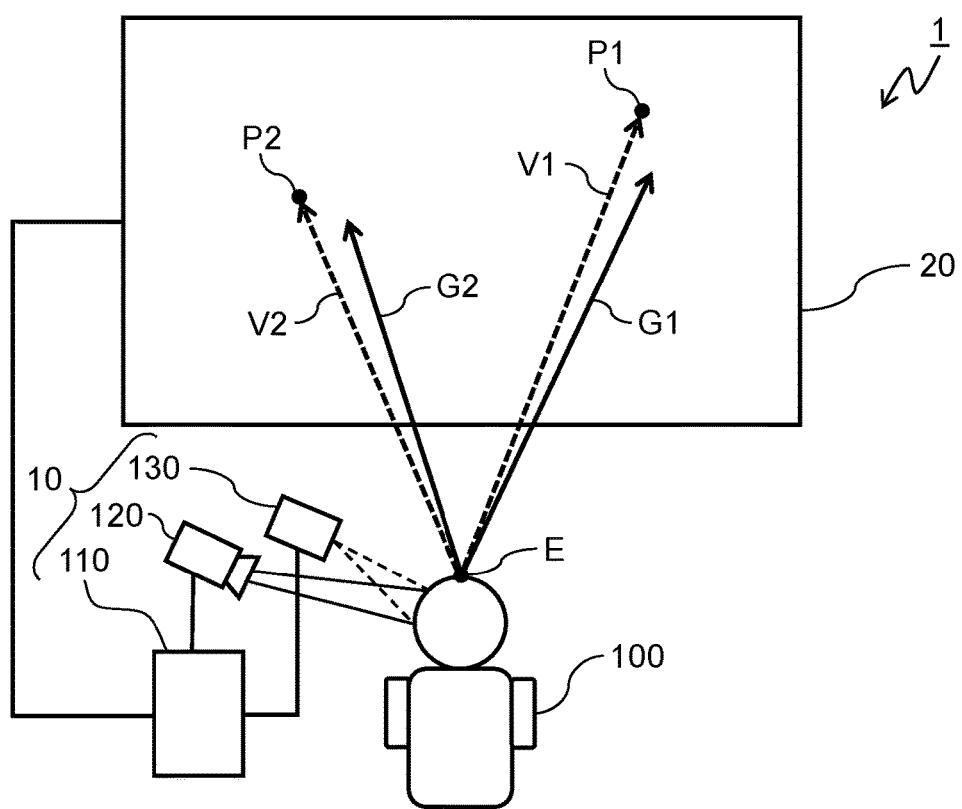
FIG. 1 is a view illustrating a configuration example of an eye tracking system according to a first exemplary embodiment.

FIG. 1 is a view illustrating a configuration example of eye tracking system 1 according to a first exemplary embodiment.

In FIG. 1, eye tracking system 1 includes eye tracking device 10 that measures a visual line of object person 100 and display 20 that displays a gaze destination for object person 100. Further, eye tracking device 10 includes image-capturing unit 120 that captures a facial image (eyeball image) of object person 100, light source 130 that emits light on an eyeball (not illustrated) of object person 100, and computing device 110 that performs visual line measurement of object person 100.

Display 20 displays gaze point P1 and gaze point P2 that are used as a gaze destination of object person 100. Display 20 is only enough to be able to display the gaze destination of object person 100. Display 20 includes a display element such as a liquid crystal display (LCD) panel and an organic electroluminescence (EL) display panel and a drive circuit that drives the display element. Display 20 displays gaze points P1, P2 under control of eye tracking device 10 or a controller (not illustrated).

Light source 130 is disposed at a predetermined position and emits light to form a corneal reflex point on the eyeball of object person 100. For example, light source 130 is a light source that emits infrared light.

Image-capturing unit 120 captures the facial image of object person 100 that reflects the light emitted from light source 130. For example, image-capturing unit 120 is an infrared camera. Image-capturing unit 120 captures the facial image of object person 100 by receiving the reflected light of the infrared light emitted from light source 130.

In advance of actual visual line measurement, computing device 110 detects a visual line vector (calculative visual line vectors G1, G2) of object person 100 from the facial image of object person 100, the facial image being captured by image-capturing unit 120. Then, computing device 110 calculates correction information for correcting an individual difference from a correlation between real visual line vectors V1, V2 obtained from an eyeball position E (pupil center) of object person 100 and gaze points P1, P2 and calculative visual line vectors G1, G2. Computing device 110 corrects detected calculative visual line vectors G1, G2 using the calculated correction information.

[1-2. Configuration of Computing Device 110]

Figure 2:
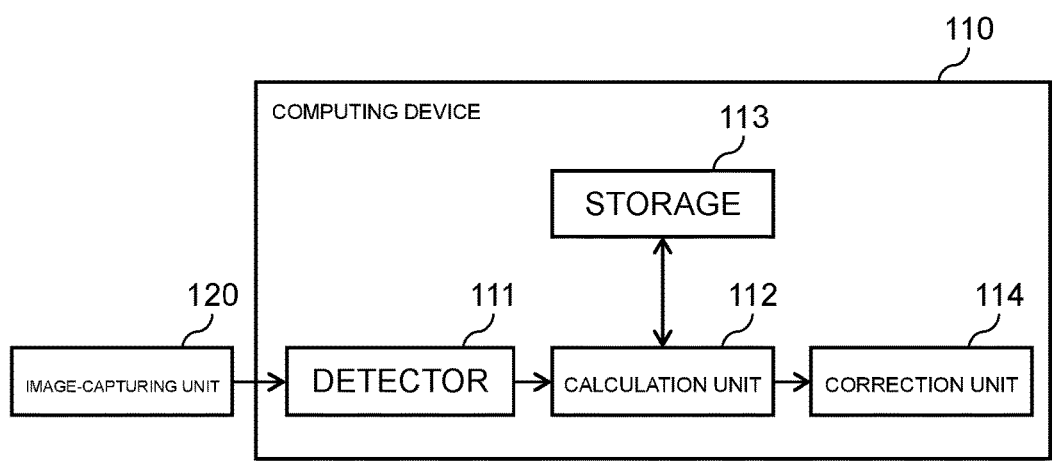
FIG. 2 is a block diagram illustrating a configuration example of a computing device of the first exemplary embodiment.

FIG. 2 is a block diagram illustrating a configuration example of computing device 110. In FIG. 2, computing device 110 includes detector 111, calculation unit 112, storage 113, and correction unit 114. Each functional unit is implemented by causing a central processing unit (CPU) to execute a program stored in a storage device such as ROM, a magnetic disk, and an optical disk.

Detector 111 calculates calculative visual line vectors G1, G2 of object person 100 using the facial image captured by image-capturing unit 120. Detector 111 also calculates real visual line vectors V1, V2 from a positional relationship between eyeball position E of object person 100 and gaze points P1, P2. Detector 111 transmits the calculated visual line vectors (the calculative visual line vector and the real visual line vector), eyeball position E of object person 100, and identification information (hereinafter, referred to as ID) that can uniquely identify object person 100 to calculation unit 112 as visual line information.

Calculation unit 112 stores the visual line information transmitted from detector 111 in storage 113. Calculation unit 112 calculates correction information to correct a detection error caused by the individual difference of the eyeball using the visual line information stored in storage 113. Calculation unit 112 outputs the visual line information and the correction information to correction unit 114.

Storage 113 stores the visual line information and the correction information. Storage 113 may be constructed with a semiconductor memory, a volatile memory, a nonvolatile memory, or the like.

Correction unit 114 corrects the visual line information calculated by detector 111 using the correction information calculated by calculation unit 112.

[1-3. Error Caused by Individual Difference of Eyeball]

Figure 3:
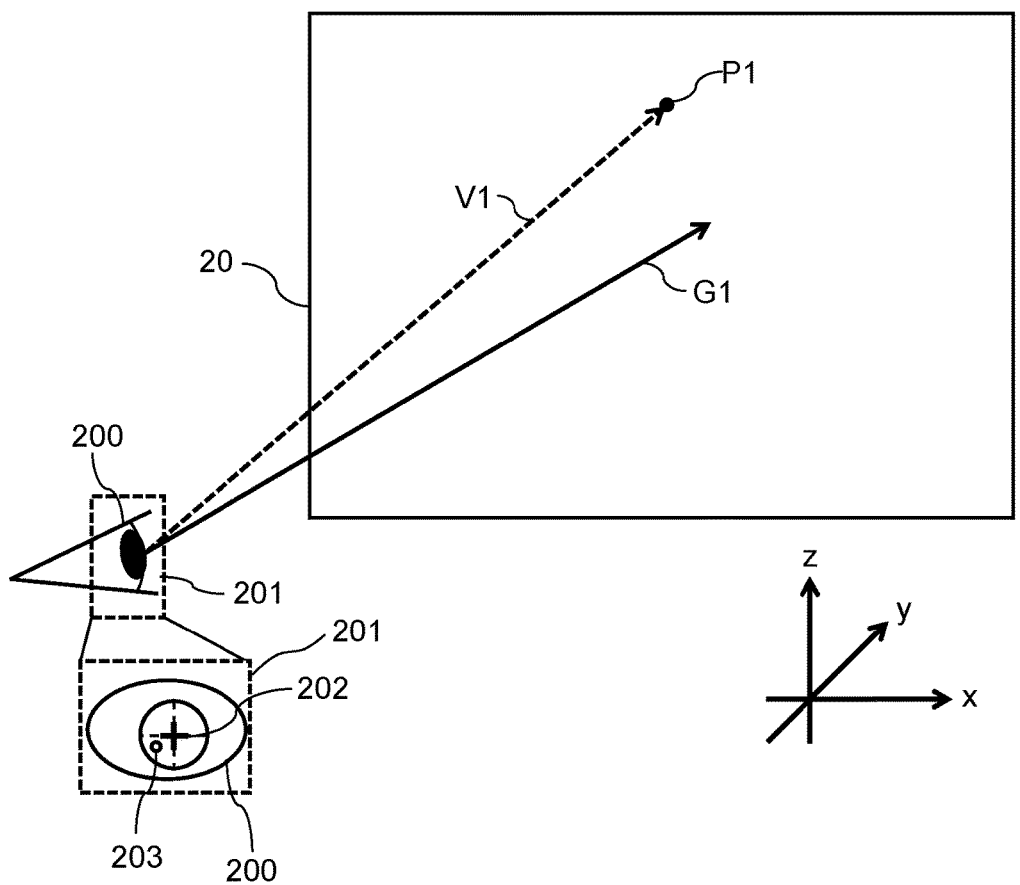
FIG. 3 is a view illustrating visual line information of the first exemplary embodiment.

FIG. 3 is a view illustrating the visual line information. In display 20 of FIG. 3, it is assumed that a center is an origin, a horizontal direction is an x-axis, a vertical direction is a z-axis, and a front-back direction is a y-axis. Such an orthogonal coordinate system in FIG. 3 is referred to as a world coordinate system.

FIG. 3 illustrates a state in which gaze point P1 of which position is known is displayed on display 20, and object person 100 gazes at gaze point P1. As used herein, as illustrated in FIG. 3, a visual line of object person 100 is defined by a visual line vector (real visual line vector V1) extending from pupil center 202 toward gaze point P1 on display 20 in pupil region 201 existing in eyeball 200 of object person 100.

Calculative visual line vector G1 of object person 100, which is calculated by detector 111 through a visual line detection method represented by a corneal reflection method and the like, is a vector including an error caused by the individual difference of object person 100. As illustrated in FIG. 3, calculative visual line vector G1 is different from real visual line vector V1. Here, pupil region 201 is detected through a technique such as clustering or elliptic approximation, and a center coordinate of pupil region 201 is obtained, accordingly pupil center 202 is obtained. As illustrated in FIG. 3, Purkinje image 203 that is the reflected light of the light emitted from light source 130 exists on eyeball 200 of object person 100.

As used herein, as illustrated in FIG. 3, the individual difference of object person 100 is caused by a light refractive index at a corneal surface of eyeball 200 of object person 100, refraction due to eye glasses and the like, an eyeball shape, and a deviation of an eyeball center from a central fossa. In correction processing (to be described later), the detection error caused by those factors is reduced using the correction information unique to the individual.

[1-4. Correction Information]

In the present disclosure, the corneal reflection method will be described as the visual line detection method. The corneal reflection method is a technique for calculating the visual line from a positional relationship between a pupil position and a Purkinje image.

In the corneal reflection method, in advance of the visual line measurement, the correction information is calculated based on a correlation between the visual line vector, which is calculated from the facial image obtained by capturing the object person who gazes at a known point, and the actual visual line vector. The corneal reflection x method is a technique for correcting the visual line vector calculated during the visual line measurement using the correction information (correction value) including a coefficient and a constant term (adding value) with respect to an angle by the following equation (Mathematical Formula 1).

$$A = \begin{pmatrix} rA \\ \theta A \\ \phi A \\ 1 \end{pmatrix} = HB = \begin{pmatrix} 1 & 0 & 0 & 0 \\ 0 & \omega 1 & 0 & \omega 2 \\ 0 & 0 & \omega 3 & \omega 4 \\ 0 & 0 & 0 & 1 \end{pmatrix} \begin{pmatrix} rB \\ \theta B \\ \phi B \\ 1 \end{pmatrix} = \quad \text{[Mathematical Formula 1]}$$

-continued $$\begin{pmatrix} rB \\ \omega 1\theta B + \omega 2 \\ \omega 3\phi B + \omega 4 \\ 1 \end{pmatrix}$$

In the corneal reflection method, in the case that elevation angle θB and azimuth angle φB of pre-correction visual line vector B are corrected into elevation angle θA and azimuth angle φA of post-correction visual line vector A, the correction information about an angle of the visual line vector is defined as matrix H in the equation (Mathematical Formula 1). In this case, information obtained when object person 100 gazes at a plurality of gaze points is required to obtain the correction information. In the present disclosure, information obtained when object person 100 gazes at gaze points P1, P2 is used to obtain the correction information.

2. Operation

As illustrated in FIG. 1, the case where gaze points P1, P2 are sequentially displayed on display 20 and object person 100 is caused to gaze at gaze points P1, P2 will be described as an example.

[2-1. Whole Operation]

Figure 4:
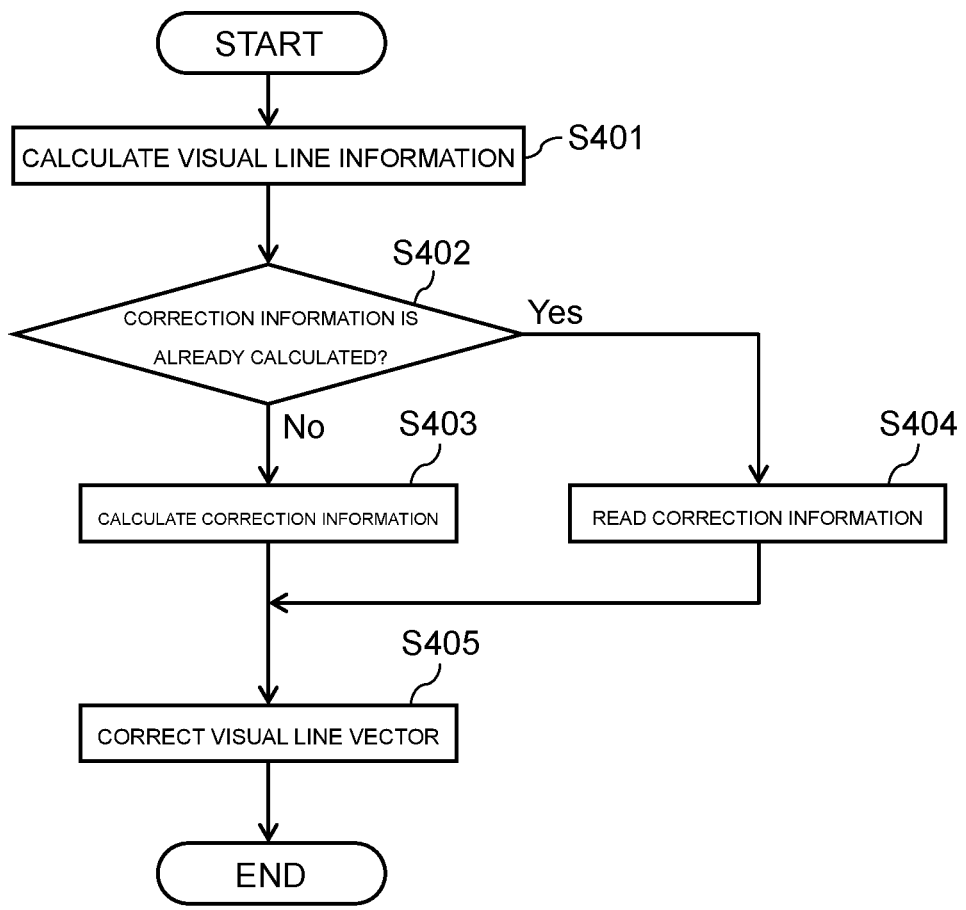
FIG. 4 is a flowchart for illustrating operation of an eye tracking device of the first exemplary embodiment.

FIG. 4 is a flowchart illustrating operation of eye tracking device 10 of the first exemplary embodiment.

(Step S401) Detector 111 performs visual line detection processing of calculating a calculative visual line vector of object person 100 using a facial image captured by image-capturing unit 120 when object person 100 gazes at gaze points P1, P2. Detector 111 calculates a real visual line vector from the positional relationship between pupil center 202 of object person 100 and gaze points P1, P2. Detector 111 correlates a pair of calculative and real visual line vectors corresponding to one gaze point with ID uniquely indicating object person 100, and transmits the resultant information to calculation unit 112 as the visual line information.

(Step S402) Calculation unit 112 stores the received visual line information in storage 113. Storage 113 checks whether the correction information corresponding to object person 100 is already calculated using the ID. As a result, the processing goes to step S404 when the correction information about object person 100 exists, that is, when the correction information about object person 100 is already calculated (Yes in step S402), and the processing goes to step S403 when the correction information about object person 100 is not calculated (No in step S402).

(Step S403) Calculation unit 112 performs correction information calculation processing of calculating the correction information about the individual difference of the visual line using the visual line information calculated by detector 111. Calculation unit 112 stores the calculated correction information in storage 113 while correlating the correction information with the ID. Calculation unit 112 transmits the visual line information and the calculated correction information to correction unit 114. When at least two sets of visual line information each of which includes a different pair of real and calculative visual line vectors are not stored in storage 113, calculation unit 112 does not calculate the correction information, but transmits an average correction value as the correction information to correction unit 114 together with the visual line information.

(Step S404) Calculation unit 112 reads the correction information correlated with the ID received from storage 113, and transmits the correction information to correction unit 114 together with the visual line information.

(Step S405) Correction unit 114 performs correction processing of correcting the calculative visual line vector using the equation (Mathematical Formula 1) based on the visual line information and correction information, which are transmitted from calculation unit 112, and calculates the post-correction visual line vector (corrected visual line vector).

Each processing will be described in detail below.

[2-2. Visual-Line Detection Processing]

The case where gaze point P1 is displayed on display 20 will be described as an example with reference to FIG. 3.

Image-capturing unit 120 captures the facial image of object person 100 who gazes at gaze point P1 on display 20, and transmits image data to detector 111. Any image-capturing timing can be set, and image-capturing timing may be controlled by a signal transmitted from a separately-disposed external device.

Detector 111 obtains an eyeball image in which a portion near the eyeball of object person 100 is cut out from the facial image captured by image-capturing unit 120. Image-capturing unit 120 may capture the facial image of object person 100 such that the facial image includes only one eye or both eyes. Detector 111 may obtain the eyeball image of only one eye or both the eyes as the eyeball image of object person 100. The eye of object person 100 indicates an eyeball surface including an iris, white of the eye, and an eyelid.

Then, as illustrated in FIG. 3, detector 111 calculates calculative visual line vector G1 through the corneal reflection method using the positional relationship among pupil center 202 of object person 100, Purkinje image 203, image-capturing unit 120, and light source 130.

At this point, it is assumed that three-dimensional positions of image-capturing unit 120 and light source 130, which are required to calculate calculative visual line vector G1, are obtained as the known point, and previously stored in a storage (not illustrated) of visual line measuring device 10. The three-dimensional positions of pupil center 202 of object person 100 and Purkinje image 203 may be obtained using a stereo camera or through a distance measuring method other than the stereo camera. The three-dimensional positions of pupil center 202 of object person 100 and Purkinje image 203 are also stored in storage 113.

Specifically, detector 111 cuts out pupil region 201 from the facial image of object person 100 captured by image-capturing unit 120 when object person 100 gazes at gaze point P1 on display 20. Detector 111 calculates calculative visual line vector G1 of object person 100 based on the positions of image-capturing unit 120 and light source 130 and the positions of pupil center 202 and Purkinje image 203. Detector 111 also calculates real visual line vector V1 from the positional relationship between pupil center 202 and gaze point P1, in three dimensions, of object person 100.

Detector 111 performs the similar processing in the case that gaze point P2 is displayed on display 20 as illustrated in FIG. 1, and calculates calculative visual line vector G2 and real visual line vector V2. Thus, two pairs of the real visual line vector and the calculative visual line vector are calculated, the two pairs corresponding to the two different points of gaze points P1, P2, respectively.

When ending the calculation of the visual line vector and the real visual line vector, detector 111 transmits the pairs of the real visual line vector and the calculative visual line vector as the visual line information to calculation unit 112 while correlating the pairs of the real visual line vector and the calculative visual line vector with the positional information of object person 100 and the ID of object person 100.

[2-3. Correction Information Calculation Processing]

Calculation unit 112 statistically calculates the correction information about the individual difference of the visual line using the pairs of the real visual line vector and the calculative visual line vector corresponding to gaze points P1, P2, respectively.

Sometimes, the accurate correction information cannot be calculated depending on dispositions of gaze points P1, P2 gazed at by object person 100. Specifically, the correction information cannot be calculated in the case that gaze points P1, P2 are parallel to each other on a certain axis. This is because the correction information is calculated using a difference in angle between gaze points P1, P2.

Calculation unit 112 transforms the coordinate values of gaze points P1, P2 in the world coordinate system into the coordinate values in the correction coordinate system, and transforms the positional relationship between gaze points P1, P2 into the positional relationship from which the correction information can be calculated.

Figure 6A:
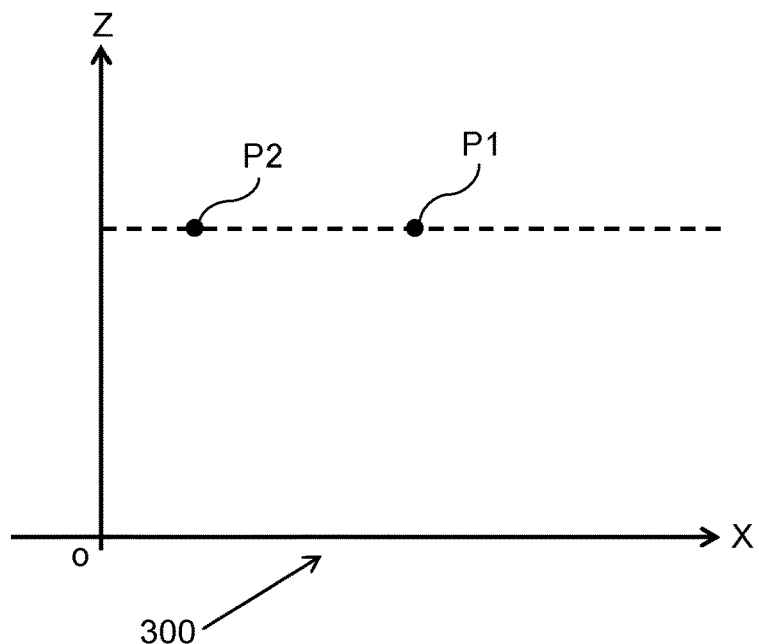
FIG. 6A is a view illustrating a positional relationship between two gaze points in a world coordinate system of the first exemplary embodiment.
Figure 6B:
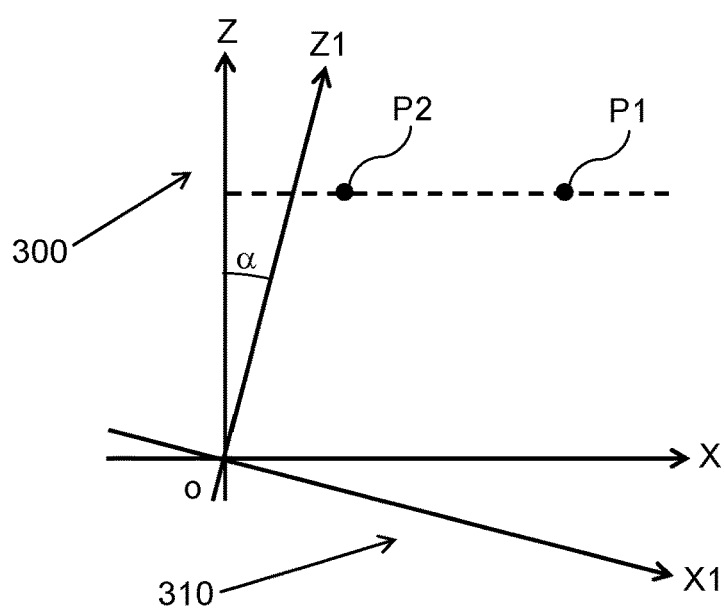
FIG. 6B is a view illustrating a positional relationship between two gaze points in a correction coordinate system of the first exemplary embodiment.

FIG. 6A is a view illustrating the positional relationship between gaze points P1, P2 in the world coordinate system. FIG. 6B is a view illustrating the positional relationship between gaze points P1, P2 in the correction coordinate system. As illustrated in FIG. 6B, correction coordinate system 310 is an orthogonal coordinate system, which has the same origin as world coordinate system 300 and includes an X1-axis, a Y1-axis, and a Z1-axis in which the world coordinate system is rotated about a Y-axis by rotation amount $\alpha$. As illustrated in FIGS. 6A and 6B, gaze points P1, P2 having the positional relationship parallel to an X-axis on world coordinate system 300 do not have the positional relationship parallel to the X1-axis on correction coordinate system 310. Calculation unit 112 calculates the correction value unique to the individual using the angle (the elevation angle and the azimuth angle) of each visual line vector with respect to the reference direction in the correction coordinate system after coordinate transformation.

Figure 5:
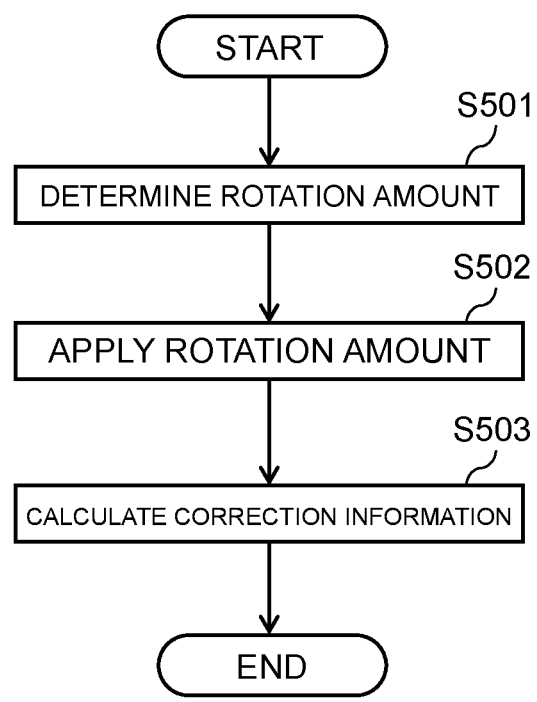
FIG. 5 is a flowchart illustrating operation of a calculation unit of the first exemplary embodiment.

FIG. 5 is a flowchart illustrating operation of calculation unit 112 of eye tracking device 10.

(Step S501) Calculation unit 112 calculates rotation amount $\alpha$ from the positional relationship between gaze points P1, P2 on display 20 in transforming the world coordinate system into the correction coordinate system.

In the first exemplary embodiment, it is assumed that rotation amount $\alpha$ is a roll angle. Other than the roll angle, rotation amount $\alpha$ may be another rotation angle such as a yaw angle and a pitch angle or a rotation amount in which at least two of these angles are combined. That is, rotation amount $\alpha$ is the rotation amount of one of the coordinate axes of the world coordinate system or at least two coordinate axes.

(Step S502) Calculation unit 112 applies calculated rotation amount $\alpha$ to real visual line vectors V1, V2 and calculative visual line vectors G1, G2 to transform each vector from the world coordinate system into the correction coordinate system.

(Step S503) Calculation unit 112 transforms real visual line vectors V1, V2 and calculative visual line vectors G1, G2 from the coordinate value in the correction coordinate system into the angle. Calculation unit 112 calculates the correction information using the angle relationship of real visual line vector V1 and calculative visual line vector G1 with respect to gaze point P1 and the angle relationship of real visual line vector V2 and calculative visual line vector G2 with respect to gaze point P2.

[2-4. Correction Processing]

Correction unit 114 performs the correction processing on the calculative visual line vector detected by detector 111 after transforming the calculative visual line vector into the correction coordinate system similarly to the calculation of the correction information, and transforms the calculative visual line vector into the world coordinate system again to calculate the post-correction visual line vector (corrected visual line vector).

[2-5. Specific Example]

Figure 7:
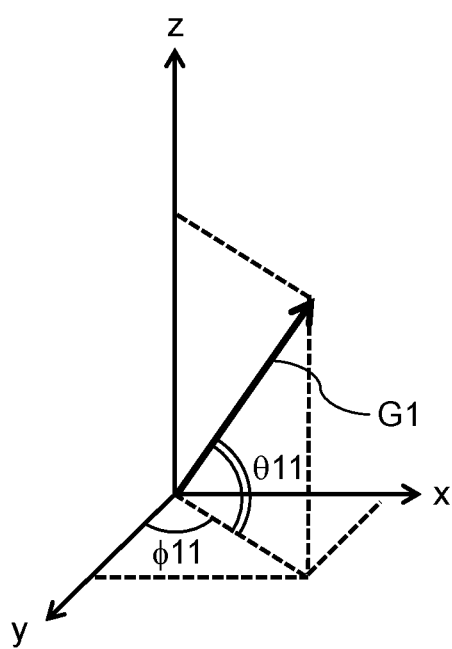
FIG. 7 is a view illustrating an angle of a visual line vector of the first exemplary embodiment.

The case where the visual line of object person 100 is measured while gaze points P1, P2 are sequentially displayed on display 20 will be described below with reference to FIGS. 1, 2, 7. FIG. 7 is a view illustrating an angle of the visual line vector.

Gaze point P1 is displayed on display 20, and object person 100 is caused to gaze at gaze point P1. Image-capturing unit 120 captures the image of object person 100 who gazes at gaze point P1. Detector 111 obtains the eyeball image from the facial image captured by image-capturing unit 120, and calculates calculative visual line vector G1 from the eyeball image.

Calculative visual line vector G1 is represented as a vector in a polar coordinate system as indicated by the following equation (Mathematical Formula 2).

$$G1 = \begin{pmatrix} r11 \\ \theta 11 \\ \phi 11 \\ 1 \end{pmatrix}$$ [Mathematical Formula 2]

In the equation (Mathematical Formula 2), diameter r11 is a diameter of the vector, and is a distance from pupil center 202 to gaze point P1 on display 20. Diameter r11 of the vector may be set to one as a unit vector. For example, as illustrated in FIG. 7, deflection angle $\theta 11$ is an angle formed between calculative visual line vector G1 and a xy-plane in the world coordinate system. For example, as illustrated in FIG. 7, deflection angle $\varphi 11$ is an angle formed between calculative visual line vector G1 and a reference axis (y-axis) in the world coordinate system.

Other than the angle formed between calculative visual line vector G1 and the reference axis in the world coordinate system, for example, deflection angle $\theta 11$ and deflection angle $\varphi 11$ may be an angle formed between image-capturing unit 120 and the reference axis of the coordinate system determined by the positional relationship between light source 130 and pupil center 202 of object person 100.

Detector 111 calculates real visual line vector V1 based on the position of gaze point P1 on display 20 and pupil center 202. Similarly to calculative visual line vector G1, real visual line vector V1 is represented as the vector in the polar coordinate system as indicated by the following equation (Mathematical Formula 3).

$$V1 = \begin{pmatrix} r12 \\ \theta 12 \\ \phi 12 \\ 1 \end{pmatrix}$$ [Mathematical Formula 3]

In the equation (Mathematical Formula 3), diameter r12 is a diameter of the vector. Diameter r12 of the vector may be set to one as a unit vector. For example, deflection angle θ12 is an angle formed between real visual line vector V1 and the xy-plane in the world coordinate system. For example, deflection angle φ12 is an angle formed between real visual line vector V1 and the reference axis (y-axis) in the world coordinate system.

Next, gaze point P2 is displayed on display 20, and object person 100 is caused to gaze at gaze point P2. Image-capturing unit 120 captures the image of object person 100 who gazes at gaze point P2. Detector 111 obtains the eyeball image from the facial image captured by image-capturing unit 120, and calculates calculative visual line vector G2 from the eyeball image.

Calculative visual line vector G2 is represented as the vector in the polar coordinate system as indicated by the following equation (Mathematical Formula 4).

$$G2 = \begin{pmatrix} r21 \\ \theta 21 \\ \phi 21 \\ 1 \end{pmatrix}$$ [Mathematical Formula 4]

In the equation (Mathematical Formula 4), diameter r21 is a diameter of the vector. Diameter r21 of the vector may be set to one as a unit vector. For example, deflection angle θ21 is an angle formed between calculative visual line vector G2 and the xy-plane in the world coordinate system. For example, deflection angle φ21 is an angle formed between calculative visual line vector G2 and the reference axis (y-axis) in the world coordinate system.

Detector 111 calculates real visual line vector V2 based on the position of gaze point P2 on display 20 and pupil center 202. Similarly to calculative visual line vector G2, real visual line vector V2 is represented as the vector in the polar coordinate system as indicated by the following equation (Mathematical Formula 5).

$$V2 = \begin{pmatrix} r22 \\ \theta 22 \\ \phi 22 \\ 1 \end{pmatrix}$$ [Mathematical Formula 5]

In the equation (Mathematical Formula 5), diameter r22 is a diameter of the vector. Diameter r22 of the vector may be set to one as a unit vector. For example, deflection angle θ22 is an angle formed between real visual line vector V2 and the xy-plane in the world coordinate system. For example, deflection angle θ22 is an angle formed between real visual line vector V2 and the reference axis (y-axis) in the world coordinate system.

Detector 111 transmits the visual line information to calculation unit 112, the visual line information including a pair of the real visual line vector and calculative visual line vector calculated at gaze points P1, P2, the eyeball position, and the ID of object person 100.

Using the ID of the visual line information, calculation unit 112 checks whether the correction information of object person 100 corresponding to the ID is stored in storage 113. When the correction information is stored in storage 113, calculation unit 112 reads the visual line information received from detector 111 and the correction information stored in storage 113, and transmits the visual line information and the correction information to correction unit 114.

When the correction information of object person 100 is not stored in storage 113, that is, when the correction information is not calculated, calculation unit 112 calculates the correction information.

In this case, calculation unit 112 records the visual line information transmitted from detector 111 in storage 113, and calculates the correction information about the individual visual line using the visual line information recorded in storage 113. The position of light source 130 may be recorded in storage 113.

Calculation unit 112 reads the visual line information recorded in storage 113 using the ID, and performs the correction information calculating processing. When the visual line vector calculated at two gaze points is not included in the visual line information, calculation unit 112 does not calculate the correction information. In this case, calculation unit 112 may transmit the average correction value as the correction information to correction unit 114.

Calculation unit 112 determines rotation amount α from the visual line vector calculated at the two gaze points in order to transform the world coordinate system into the correction coordinate system. Specifically, calculation unit 112 calculates differences dθ and dφ in angle between real visual line vector V1 in gazing at gaze point P1 and real visual line vector V2 in gazing at gaze point P2. From the equation (Mathematical Formula 3) and the equation (Mathematical Formula 5), dθ is a difference between θ12 and θ22, and dφ is a difference between φ12 and φ22. In the case that dθ or dφ is less than or equal to a predetermined angle, calculation unit 112 obtains rotation amount α such that both dθ and dφ become the predetermined angle or more. For example, in the case that gaze points P1, P2 are horizontally lined up, dθ and dφ can be maximized by setting rotation amount α to 45 degrees. In the case that dθ and dφ are greater than or equal to the predetermined angle, rotation amount α may be set to zero, or rotation amount α may be obtained such that dθ and dφ become larger.

Based on rotation amount α, calculation unit 112 transforms real visual line vectors V1, V2 and calculative visual line vectors G1, G2 from the world coordinate system into the correction coordinate system.

Calculation unit 112 calculates ω1, ω2, ω3, and ω4 in matrix H indicated in the equation (Mathematical Formula 1) using a pair of calculative visual line vector G1 and real visual line vector V1 and a pair of calculative visual line vector G2 and real visual line vector V2. For example, calculation unit 112 calculates matrix H that is the correction information by substituting real visual line vector V1 in visual line vector A after correction and by substituting calculative visual line vector G1 in visual line vector B before correction in the equation (Mathematical Formula 1). A least squares method in which an error between the calculative visual line vector and the real visual line vector is minimized may be used as the calculation method. After calculating matrix H, calculation unit 112 outputs the visual line information and the calculated correction information.

Correction unit 114 corrects the calculative visual line vector using the visual line information, the correction information, and the equation (Mathematical Formula 1), and calculates the corrected visual line vector. Correction unit 114 outputs the corrected visual line vector.

3. Advantageous Effects

In visual line measuring device 10 of the present disclosure, light source 130 emits the light to form the corneal reflex point on the eyeball of object person 100 who gazes at a predetermined gaze point, and image-capturing unit 120 captures the facial image of object person 100, by which the light from light source 130 is reflected. Detector 111 calculates the visual line information in the world coordinate system using the facial image captured by image-capturing unit 120. After transforming the visual line information detected by detector 111 into the visual line information in the correction coordinate system that is the coordinate system different from the world coordinate system, correction unit 114 corrects the visual line information using the correction information for correcting the detection error caused by the individual difference of the eyeball.

Consequently, even if gaze points P1, P2 to be gazed at have a parallel relationship on a certain axis, calculation unit 112 can calculate the correction information.

Thus, the correction information about the visual line vector unique to the individual can be calculated without being affected by the positional relationship between gaze points P1, P2 to be gazed. That is, a freedom degree of the disposition of the gaze point necessary for the calculation of the correction information can be increased.

In the first exemplary embodiment, gaze points P1, P2 used to calculate the correction information are displayed on display 20. However, two gaze points can be set onto an object, which is located in front of the object person and of which the position is known. For example, for a vehicle, a traffic signal located in front of the vehicle or a speed meter in the vehicle can be used as a gaze point.

In this case, gaze points P1, P2 are assumed to be set at a center of two objects located in front of object person 100. However, in the case that points or regions at which object person 100 often gazes in the two objects are clear, gaze points P1, P2 may be set to an average position of the points or regions. In the subsequent processing, the calculation of the real visual line vector and calculative visual line vector, the decision of rotation amount α, and the calculation of the correction values are performed similarly to the case that the calculation is performed using the gaze points on display 20.

Other Exemplary Embodiments

As described above, the first exemplary embodiment is described as illustration of the technique disclosed in this application. However, the technique of the present disclosure is not limited to the first exemplary embodiment, but can be applied to exemplary embodiments in which modifications, replacements, additions, omissions, and the like are made. In addition, components described in the first exemplary embodiment can be combined to make a new exemplary embodiment. Other exemplary embodiments will be described below.

Although one light source is used in first exemplary embodiment, a plurality of light sources may be used.

In first exemplary embodiment, the gaze point is displayed on display 20 in order to cause object person 100 to gaze at the gaze point. What is displayed on display 20 is not limited to the point. However, for example, a content may be displayed at a reference position to induce object person 100 to gaze at the content. In this case, the calculation may be performed using the reference position in the content as the gaze point.

The visual line information calculated by eye tracking device 10 may be displayed on display 20. In this case, an intersection between the calculated visual line vector and display 20 may be calculated, and output as gaze destination information.

In the first exemplary embodiment, calculation unit 112 generates the correction information using two sets of visual line information. Alternatively, calculation unit 112 may select at least three sets of visual line information, and calculate the correction information using all the sets of visual line information. Final correction information may be generated based on a plurality of sets of correction information calculated by combining two sets of visual line information. For example, the plurality of sets of correction information calculated by combining two sets of visual line information may be averaged. Consequently, accuracy of the correction information can be improved.

INDUSTRIAL APPLICABILITY

The present disclosure is applicable to a visual line detection device that measures a visual line in a non-contact manner. Specifically, the present disclosure is applicable to a behavior analysis of an object person such as monitoring of a driver in a vehicle, operation of an apparatus in which the visual line is used, or other applications.

REFERENCE MARKS IN THE DRAWINGS

1: eye tracking system
10: eye tracking device
20: display
110: computing device
111: detector
112: calculation unit
113: storage
114: correction unit
120: image-capturing unit
130: light source
200: eyeball
201: pupil region
202: pupil center
203: Purkinje image
300: world coordinate system
310: correction coordinate system
G1, G2: calculative visual line vector
H: matrix
P1, P2: gaze point
V1, V2: real visual line vector

The invention claimed is:

1. An eye tracking device, comprising: a light source that emits light to form a corneal reflex point on an eyeball of an object person who gazes least two gaze points, the at least two gaze points including a first gaze point and a second gaze point, a position of the second gaze point being different from a position of the first gaze point; a camera that captures at least two facial images, each including the eyeball of the object person, in which the light emitted from the light source is reflected, the at least two facial images including a first facial image in which the object person gazes at the first gaze point and a second facial image in which the object person gazes at the second gaze point; a processor; and a memory including a set of instructions that, when executed by the processor, causes the processor to perform operations including: calculating a first calculative visual line vector and a second calculative visual line vector in a world coordinate system based on the first facial image and the second facial image, respectively; calculating a first real visual line vector and a second real visual line vector in the world coordinate system based on a first relationship between a position of the eyeball and the first gaze point and a second relationship between the position of the eyeball and the second gaze point, respectively; determining a rotation amount based on an angle relationship between the first real visual line vector and the second real visual line vector in the world coordinate system; transforming the first calculative visual line vector and the second calculative visual line vector in the world coordinate system into a third calculative visual line vector and a fourth calculative visual line vector in a correction coordinate system based on the rotation amount, the correction coordinate system being different from the world coordinate system, calculating correction information based on angle relationships between the first calculative visual line vector and the first real visual line vector and between the second calculative visual line vector and the second real visual line vector; and correcting the third calculative visual line vector and the fourth calculative visual line vector in the correction coordinate system based on the correction information.

2. The eye tracking device according to claim 1, wherein the first gaze point and the second gaze point are points displayed on a display disposed in front of the object person, or points on an object existing in front of the object person.

3. The eye tracking device according to claim 1, wherein the angle relationship between the first real visual line vector and the second real visual line vector in the world coordinate system includes: an elevation angle difference between the first real visual line vector and the second real visual line vector; and an azimuth angle difference between the first real visual line vector and the second real visual line vector.

4. The eye tracking device according to claim 1, wherein the rotation amount is of one of coordinate axes of the world coordinate system, or two or more of the coordinate axes.

5. The eye tracking device according to claim 1, wherein the correction information includes a coefficient and an adding value with respect to angles of the third calculative visual line vector and the fourth calculative visual line vector in the correction coordinate system.

6. The eye tracking device according to claim 1, wherein the operations further include:
    transforming the corrected third calculative visual line vector and the corrected fourth calculative visual line vector in the correction coordinate system into a fifth calculative visual line vector and a sixth calculative visual line vector in the world coordinate system; and
    calculating post-correction information based on the fifth calculative visual line vector and the sixth calculative visual line vector in the world coordinate system.

7. The eye tracking device according to claim 6, wherein the operations further include:
    correcting the first real visual line vector and the second real visual line vector based on the post-correction information, to define a first post-correction real visual line vector and a second post-correction real visual line vector.

8. The eye tracking device according to claim 7, wherein, in the correcting of the first real visual line vector and the second real visual line vector based on the post-correction information, an elevation angle and an azimuth angle of each of the first real visual line vector and the second real visual line vector is corrected.

9. The eye tracking device according to claim 8, wherein the operations further include:
    correcting a detection error caused by an individual difference of the eyeball of the object person via the first post-correction real visual line vector and the second post-correction real visual line vector.

10. The eye tracking device according to claim 1, wherein a segment interconnecting the first gaze point and the second gaze point is parallel to an axis of the a world coordinate system.

11. An eye tracking method, comprising: capturing, by a camera, at least two facial images, each including an eyeball of an object person, in which light from a light source that emits the light to form a corneal reflex point on the eyeball of the object person who gazes at least two gaze points is reflected from the eyeball, the at least two gaze points including a first gaze point and a second gaze point, a position of the second gaze point being different from a position of the first gaze point, the at least two facial images including a first facial image in which the object person gazes at the first gaze point and a second facial image in which the object person gazes at the second gaze point; calculating a first calculative visual line vector and a second calculative visual line vector in a world coordinate system based on the first facial image and the second facial image, respectively; calculating a first real visual line vector and a second real visual line vector in the world coordinate system based on a first relationship between a position of the eyeball and the first gaze point and a second relationship between the position of the eyeball and the second gaze point, respectively; determining a rotation amount based on an angle relationship between the first real visual line vector and the second real visual line vector in the world coordinate system; transforming the first calculative visual line vector and the second calculative visual line vector in the world coordinate system into a third calculative visual line vector and a fourth calculative visual line vector in a correction coordinate system based on the rotation amount, the correction coordinate system being different from the world coordinate system, calculating correction information based on angle relationships between the first calculative visual line vector and the first real visual line vector and between the second calculative visual line vector and the second real visual line vector; and correcting the third calculative visual line vector and the fourth calculative visual line vector in the correction coordinate system based on the correction information.

12. The eye tracking method according to claim 11, further comprising:
    transforming the corrected third calculative visual line vector and the corrected fourth calculative visual line vector in the correction coordinate system into a fifth calculative visual line vector and a sixth calculative visual line vector in the world coordinate system; and
    calculating post-correction information based on the fifth calculative visual line vector and the sixth calculative visual line vector in the world coordinate system.

13. The eye tracking method according to claim 12, further comprising:
    correcting the first real visual line vector and the second real visual line vector based on the post-correction information, to define a first post-correction real visual line vector and a second post-correction real visual line vector.

14. The eye tracking method according to claim 13, wherein, in the correcting of the first real visual line vector and the second real visual line vector based on the post-correction information, an elevation angle and an azimuth angle of each of the first real visual line vector and the second real visual line vector is corrected.

15. The eye tracking method according to claim 14, further comprising:
    correcting a detection error caused by an individual difference of the eyeball of the object person via the first post-correction real visual line vector and the second post-correction real visual line vector.

16. The eye tracking method according to claim 11, wherein a segment interconnecting the first gaze point and the second gaze point is parallel to an axis of the a world coordinate system.

17. An eye tracking device comprising:
    a light source that emits light to form a corneal reflex point on an eyeball of an object person who gazes at two gaze points;
    an image-capturing unit that captures two facial images including the eyeball of the object person, the light emitted from the light source being reflected from the eyeball;
    a detector that calculates two pieces of visual line information in a world coordinate system using the two facial images captured by the image-capturing unit;
    a calculation unit that determines a rotation amount based on a positional relationship between the two gaze points; and
    a correction unit that transforms, using the rotation amount when the object person gazes at each of the two gaze points, each of the two pieces of visual line information in the world coordinate system calculated by the detector into visual line information in a correction coordinate system that is a coordinate system different from the world coordinate system based on a positional relationship between two gaze points of which positions are different from each other, calculates correction information from differences between angles of the two pieces of visual line information in the correction coordinate system and angles formed between a position of the eyeball of the object person and directions of the two gaze points, and corrects the visual line information in the correction coordinate system using the correction information for correcting a detection error caused by an individual difference of the eyeball,
    wherein the calculation unit determines the rotation amount by differences between an elevation angle and an azimuth angle of visual line vectors when the object person gazes at the two gaze points.

* * * * *